(12) United States Patent
Beech, Jr. et al.

(10) Patent No.: US 9,162,942 B2
(45) Date of Patent: Oct. 20, 2015

(54) CATALYST REGENERATION PROCESS

(75) Inventors: James H. Beech, Jr., Kingwood, TX (US); Julia E. Steinheider, Houston, TX (US); Doron Levin, Highland Park, NJ (US); Selma S. Lawrence, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 96 days.

(21) Appl. No.: 13/811,403

(22) PCT Filed: Jul. 20, 2011

(86) PCT No.: PCT/US2011/044634
§ 371 (c)(1),
(2), (4) Date: Apr. 4, 2013

(87) PCT Pub. No.: WO2012/027034
PCT Pub. Date: Mar. 1, 2012

(65) Prior Publication Data
US 2013/0267748 A1    Oct. 10, 2013

Related U.S. Application Data

(60) Provisional application No. 61/377,326, filed on Aug. 26, 2010.

(51) Int. Cl.
| | | |
|---|---|---|
| C07C 6/12 | (2006.01) | |
| C07C 2/12 | (2006.01) | |
| B01J 29/90 | (2006.01) | |
| B01J 38/14 | (2006.01) | |
| B01J 38/16 | (2006.01) | |
| B01J 38/20 | (2006.01) | |
| B01J 29/08 | (2006.01) | |
| B01J 29/18 | (2006.01) | |
| B01J 29/40 | (2006.01) | |
| B01J 29/70 | (2006.01) | |
| B01J 37/18 | (2006.01) | |
| B01J 37/20 | (2006.01) | |

(52) U.S. Cl.
CPC ............. *C07C 2/12* (2013.01); *B01J 29/084* (2013.01); *B01J 29/18* (2013.01); *B01J 29/40* (2013.01); *B01J 29/70* (2013.01); *B01J 29/7007* (2013.01); *B01J 29/7034* (2013.01); *B01J 29/7038* (2013.01); *B01J 29/7042* (2013.01); *B01J 29/7046* (2013.01); *B01J 29/90* (2013.01); *B01J 38/14* (2013.01); *B01J 38/16* (2013.01); *B01J 38/20* (2013.01); *C07C 6/126* (2013.01); *B01J 37/18* (2013.01); *B01J 37/20* (2013.01); *C07C 2529/08* (2013.01); *C07C 2529/18* (2013.01); *C07C 2529/40* (2013.01); *C07C 2529/70* (2013.01)

(58) Field of Classification Search
USPC ........................................................ 585/475
See application file for complete search history.

(56) References Cited

U.S. PATENT DOCUMENTS

| | | | |
|---|---|---|---|
| 4,139,433 | A | 2/1979 | Ward |
| 4,480,144 | A | 10/1984 | Smith |
| 4,550,009 | A | 10/1985 | Burkel |
| 4,870,038 | A | 9/1989 | Page et al. |
| 4,975,399 | A | 12/1990 | Gardner |
| 5,093,293 | A | 3/1992 | Laukonen |
| 6,579,821 | B1 | 6/2003 | Ginosar et al. |
| 2003/0149321 | A1 | 8/2003 | Mees et al. |
| 2006/0100089 | A1 | 5/2006 | Ginosar et al. |
| 2010/0298117 | A1 | 11/2010 | Levin et al. |

FOREIGN PATENT DOCUMENTS

| | | |
|---|---|---|
| EP | 0 009 894 | 4/1980 |
| EP | 0 045 333 | 2/1982 |
| GB | 616793 | 7/1945 |
| WO | WO 2009067331 A2 * | 5/2009 |

OTHER PUBLICATIONS

Muller et al., "*In Situ Monitoring of Coke Deposits During Coking and Regeneration of Solid Catalysts by Electrical Impedance-Based Sensors*," Chemical Engineering and Technology, vol. 33, No. 1, pp. 103-112 (2010).

Tsai et al., "*Reactivation of Acidic Sites in Mordenite Used in Toluene Disproportionation*," Applied Catalysis A: General, vol. 301, No. 2, pp. 292-298 (2006).

* cited by examiner

*Primary Examiner* — Thuan D Dang

(57) ABSTRACT

This disclosure relates to a process for regenerating a catalyst composition to improve the aging rate in subsequent cycles.

12 Claims, No Drawings

CATALYST REGENERATION PROCESS

CROSS REFERENCE TO RELATED APPLICATIONS

This application is a National Stage Application of International Application No. PCT/US2011/044634, filed Jul. 20, 2011, which claims priority to Provisional Application No. 61/377,326, filed Aug. 26, 2010, the disclosures of which are incorporated by reference in their entireties.

FIELD OF THE INVENTION

The invention concerns regeneration of a molecular sieve catalyst, more particularly end-of-cycle conditions for regeneration of a molecular sieve use in aromatic hydrocarbon processing.

BACKGROUND OF THE INVENTION

Molecular sieves are used in numerous commercial processes for hydrocarbon conversion and/or separation, particularly the conversion and/or separation of aromatic hydrocarbons, such as transalkylation, disproportionation, isomerization, adsorptive separation, and the like. Very often the goal is to produce more xylenes from one or more of benzene, toluene, and aromatic hydrocarbons having 9 carbons or more (C9+ aromatic hydrocarbons or more simply "A9+"). For example, the production of xylenes via transalkylation of A9+ with C6 and/or C7 aromatics to produce xylenes may use a molecular sieve based catalyst such as at least one of Mordenite, ZSM-12, MCM-22 family material, and combinations thereof. Certain molecular sieves are useful to purify one or more of the feed streams upstream of the transalkylation reaction and certain molecular sieves may also be useful in separation and/or isomerization of the xylene product downstream of the transalkylation reaction.

Typically molecular sieves lose performance, such as activity, selectivity, and capacity, through various deactivation mechanisms. As the molecular sieve catalyst or adsorbent ages with increasing time on stream, more severe conditions, such as higher temperature and/or low through-put, are normally required to maintain comparable activity and/or selectivity. When the maximum reactor temperature and/or minimum acceptable through-put is reached, the molecular sieve catalyst or adsorbent needs to be replaced or regenerated/rejuvenated. The spent catalyst, at the end of its useful life, may contain a significant amount of coke, often exceeding 35 wt %, and sometimes even as high as 50 wt %. Various techniques, sometimes called regenerative or rejuvenative, are known that remove the deposited coke, in whole or in part, and allow the molecular sieve to be reused. These techniques may be performed in situ and/or ex situ, depending on the technique and other factors.

One common regeneration technique is to burn the coke from the molecular sieve in an oxidative environment, such as air or oxygen. It had been thought that the oxidative calcination process normally needed to be controlled with dry air to prevent steam damage to the molecular sieve framework, for example, steam dealumination of zeolite, which causes severe damage to the molecular sieve. Recently it was discovered that the controlled addition of water during the regeneration, combined with a staged controlled temperature burn, can successfully regenerate a heavily coked catalyst with minimal steam damage of the molecular sieve structure. See U.S. application Ser. No. 12/738,057.

Another less common regeneration technique is to rejuvenate a spent catalyst in a reductive environment, such as hydrogen. However, if the catalyst is not regenerated properly, aging rates during the second cycle can be very high resulting in a second cycle length as short as less than 10% of the first cycle length.

Other regeneration techniques include the use of steam or other solutions in combination with heating or calcining. For example, U.S. Pat. No. 5,093,293 discloses the use of steam for removing coke and other contaminants from Zeolite L, and U.S. Pat. No. 4,139,433 discloses that a hydrocracking catalyst containing a Group VIII metal is regenerated by treating the spent catalyst with an ammonium hydroxide solution followed by calcination. Still other techniques are disclosed in U.S. Pat. Nos. 4,975,399 and 4,550,009. There are no doubt a plethora of additional techniques and the aforementioned citations are intended merely to be representative thereof.

In typical commercial operations molecular sieve catalysts usually have a finite cycle time, which is the length of time over which the process is operated. The cycle time is usually determined by when the temperature required to maintain constant conversion to offset the declining activity exceeds the physical limitations of the equipment, or it may be determined by some other indicia of efficiency, such as throughput. As the catalyst approaches a certain temperature, the aging rate exponentially increases such that it is no longer efficient (e.g., viable and/or economical) to maintain operations.

The present inventors have noted that this correlates with the amount of coke on the catalyst; the more coke on the catalyst, the closer the catalyst is to reaching the defined cycle length. In addition, the present inventors have noted that this also correlates with the extent to which the coke is graphitic in nature, e.g., coke having a relatively low H/C ratio. The catalyst then needs to be regenerated or replaced. Given the cost of a new catalyst load, the preferred method of choice to regain catalyst activity is to regenerate/rejuvenate the catalyst, either in-situ or ex-situ, to remove the coke that has built up on the catalyst.

The present inventors have further discovered that the end-of-cycle condition of the molecular sieve catalyst with respect to wt % coke and/or the graphitic nature of the coke, as measure by H/C ratio, is an important factor in determining subsequent cycle performance after regeneration, and thus a better indicia of the appropriate cycle time, rather than indicia used in the prior art.

SUMMARY OF THE INVENTION

The present invention is a process comprising conversion of a hydrocarbon feed stream, including contacting said feed stream with a molecular sieve under preselected starting conditions, including a starting reactor temperature, and carrying out said contacting for a cycle time, whereby coke deposits on said catalyst during at least a portion of said cycle time and wherein the reactor temperature is increased and/or throughput is decreased over at least a portion of said cycle time in order to meet at least one predetermined indicia of conversion efficiency, the improvement comprising determining the end of cycle time by at least one of (i) wt % coke deposits on said molecular sieve, and (ii) H/C ratio of the coke deposits on said molecular sieve.

In embodiments, the process includes regenerating or rejuvenating said catalyst by treatment under oxidative conditions, reductive conditions, treatment with steam or other solutions such as ammonium hydroxide, and combinations thereof.

In embodiments, the conversion process is selected from transalkylation, disproportionation, comproportionation, isomerization, alkylation, adsorptive separation, and combinations thereof.

In embodiments, the end of cycle time is determined to be when the amount of coke on said catalyst is no more than 40 wt %, or no more than 35 wt %, based on the total weight of catalyst and coke, and/or when the H/C of the coke deposits on said catalyst is no less than about 0.42, or no less than 0.50, or no less than 0.56.

In other aspects, the coke on the catalyst prior to regeneration has a H/C ratio in the range of 0.20 to 0.67, or 0.30 to 0.60, or 0.34 to 0.55.

In embodiments, the molecular sieve catalyst is selected from Mordenite, ZSM-12, M41S, MCM-22, ZSM-5, ZSM-11, ZSM-22, ZSM-23, zeolite Beta, zeolite Y, and combinations thereof.

In an embodiment the end of cycle conditions may be determined by: (a) contacting said feed stream with a molecular sieve under preselected starting conditions, including a starting reactor temperature, and carrying out said contacting for a cycle time, whereby coke deposits on said catalyst during at least a portion of said cycle time and wherein the reactor temperature is increased and/or through-put is decreased over at least a portion of said cycle time in order to meet at least one predetermined indicia of conversion efficiency; (b) determining end of cycle conditions, including the (i) final temperature, (ii) catalyst aging rate, and at least one of (iii) the wt % of coke deposits on said catalyst and/or (iv) the carbon to hydrogen ratio of the coke deposits on said catalyst; (c) regenerating said catalyst, wherein said regenerating includes removal of at least a portion of said coke deposits on said catalyst; (d) repeating steps (a) through (c) with the proviso that at least one of the end of cycle conditions in step (b) is changed; (e) determining from (d) or by repeating step (d) a number of times sufficient to determine the desired end of cycle conditions required to increase catalyst aging rate; and then (f) operating said process under said desired end of cycle conditions.

It is an object of this invention to provide an alternative to the conversion processes using molecular sieves wherein final reactor temperature or through-put is the indicia used to stop the process for catalyst renewal, an alternative that provides improved performance over the entire life of the molecular sieve through plural cycle times.

It is an object of the invention to provide a method of improving aromatic conversion processes that use in situ or ex situ regeneration or rejuvenation of molecular sieves, whereby the catalyst aging rate from run-to-run is decreased.

These and other objects, advantages, and improvements will be become evident in view of the following detailed description.

DETAILED DESCRIPTION OF THE EMBODIMENTS

As used in this specification, the term "framework type" is used in the sense described in the "Atlas of Zeolite Framework Types," 2001.

As used herein, the numbering scheme for the Periodic Table Groups is used as in Chemical and Engineering News, Vol. 63, Issue (5), p. 27 (1985).

The term "wppm" as used herein is defined as parts per million by weight.

The term "aromatic" as used herein is to be understood in accordance with its art-recognized scope which includes alkyl substituted and unsubstituted mono- and polynuclear compounds. The term "non-aromatic" or "non-aromatics" as used herein means hydrocarbon or hydrocarbons containing no aromatic ring.

The M41S family mesoporous molecular sieve is described in J. Amer. Chem. Soc., 1992, 114, 10834. Members of the M41S family mesoporous molecular sieve include MCM-41, MCM-48 and MCM-50. A member of this class is MCM-41 whose preparation is described in U.S. Pat. No. 5,098,684. MCM-41 is characterized by having a hexagonal structure with a unidimensional arrangement of pores having a cell diameter greater than 13 Angstroms. The physical structure of MCM-41 is like a bundle of straws wherein the opening of the straws (the cell diameters of the pores) ranges from 13 to 200 Angstroms. MCM-48 has a cubic symmetry and is described, for example, in U.S. Pat. No. 5,198,203. MCM-50 has a layered or lamellar structure and is described in U.S. Pat. No. 5,246,689.

The term "MCM-22 family material" (or "material of the MCM-22 family" or "molecular sieve of the MCM-22 family"), as used herein, includes one or more of:
(i) molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth Edition, 2001);
(ii) molecular sieves made from a common second degree building block, being a 2-dimensional tiling of such MWW framework topology unit cells, forming a monolayer of one unit cell thickness, preferably one c-unit cell thickness;
(iii) molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and
(iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U.S. Pat. No. 4,954,325 and U.S. patent application Ser. No. 11/823,722), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575), UZM-8 (described in U.S. Pat. No. 6,756,030), MCM-56 (described in U.S. Pat. No. 5,362, 697), EMM-10-P (described in U.S. patent application Ser. No. 11/823,129), and EMM-10 (described in U.S. patent application Ser. Nos. 11/824,742, and 11/827,953).

It is to be appreciated the MCM-22 family molecular sieves described above are distinguished from conventional large pore zeolite alkylation catalysts, such as mordenite, in that the MCM-22 materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, PSH-3, SSZ-25, and ERB-1. Such molecular sieves are useful for alkylation of aromatic compounds. For example, U.S. Pat. No. 6,936,744 discloses a process for producing a monoalkylated aromatic compound, particularly cumene, comprising the step of contacting a polyalkylated aromatic compound with an alkylatable aromatic compound under at least partial liquid phase conditions and in the presence of a transalkylation catalyst to produce the monoalkylated aromatic compound, wherein the transalkylation catalyst comprises a mixture of at least two different crystalline molecular sieves, wherein each of said molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstrom (A).

The MCM-22 family molecular sieves including MCM-22, MCM-49, and MCM-56 have various applications in hydrocarbon conversion processes. Unfortunately, industrial applications of zeolite catalysts have been hindered due to some major disadvantages associated with the current synthesis techniques that make large scale production of these catalysts complicated and therefore expensive. At present, crystalline zeolite catalysts are synthesized mainly by conventional liquid-phase hydrothermal treatment, including in-situ crystallization and seeding method, and the liquid phase transport method.

As used herein the terms regeneration and rejuvenation take their art-recognized meaning, however it should be appreciated that for the purposes of the present invention, the distinction is not important, rather it will be understood that what is meant is renewal of the catalyst by restoring at least partially its activity, by some process. The term "regeneration" will thus be used in the claims as a generic term for this at least partial restoration of activity for the process for which the activity is intended.

In some embodiments of this disclosure, the regeneration process is useful for regenerating a catalyst composition having a molecular sieve, wherein the molecular sieve comprises at least one of a M41S family molecular sieve, a MCM-22 family molecular sieve, ETS-10, ETAS-10, ETGS-10, and a molecular sieve having a zeolite framework type comprising at least one of ABW, AET, AFG, AFI, AFX, ANA, AST, ASV, BCT, *BEA, BEC, BIK, BOG, BPH, BRE, CAN, CAS, CDO, CFI, CGS, CHA, -CHI, CON, DAC, DDR, DFT, DOH, DON, EAB, EDI, EMT, EON, EPI, ERI, ESV, ETR, EUO, EZT, FAR, FAU, FER, FRA, GIS, GIU, GME, GON, GOO, HEU, IFR, IHW, IMF, ISV, ITE, ITH, ITW, IWR, IWV, IWW, JBW, KFI, LAU, LEV, LIO, -LIT, LOS, LOV, LTA, LTL, LTN, MAR, MAZ, MEI, MEL, MEP, MER, MFI, MFS, MON, MOR, MOZ, MSE, MSO, MTF, MTN, MTT, MTW, MWW, NAB, NAT, NES, NON, NPO, NSI, OBW, OFF, OSO, OWE, -PAR, PAU, PHI, PON, RHO, -RON, RRO, RSN, RTE, RTH, RUT, RWR, RWY, SFE, SFF, SFG, SFH, SFN, SFO, SGT, SIV, SOD, SOS, SSY, STF, STI, STT, SZR, TER, THO, TOL, TON, TSC, TUN, UEI, UFI, UOZ, USI, UTL, VET, VNI, VSV, -WEN, and YUG. In a preferred embodiment, the molecular sieve useful in this disclosure comprises at least one of Mordenite, ZSM-12, MCM-22 family material, ZSM-5, ZSM-11, ZSM-22, ZSM-23, zeolite beta, and zeolite Y. The composition of this disclosure may further comprise a binder. In further embodiments of this disclosure, the composition of this disclosure may also comprise at least one metal selected from Groups 1-17, preferably Groups 3-12, more preferably Groups 6-10, of the Periodic Table of Element.

The binders which are used in preparing the catalyst compositions include clays, silica, alumina, and mixtures thereof. Specific examples of clays include attapulgite, bentonite, sepiolite, halloysite, and kaolinite. The zeolite and binder can be combined in various ratios but usually the binder is present from 10 to 90 wt % of the catalyst composition.

The catalyst composition can be formed into various shapes by means well known in the art. Generally the molecular sieve and binder are combined along with water and optionally one or more additives selected from extrusion aids, dispersion aids, porosity modifiers, peptizing agents, etc. Examples of these additives are carboxymethylcellulose (extrusion aid), sodium salt of polyacrylic acid (dispersion aid), polyethylene (porosity modifier), nitric acid (peptizing agent). The molecular sieve, water and optional additive are homogeneously mixed by mulling, kneading, etc. Once a homogeneous mixture is obtained it is formed into shapes such as extrudates, pellets, pills, beads, etc., by means well known in the art. These shaped catalyst compositions will possess the physical and chemical properties necessary for the intended use. For example, crush strength, attrition resistance, surface area, adsorption capacity, etc.

These catalyst compositions are used in various hydrocarbon conversion processes, such as toluene disproportionation, comproportionation, transalkylation, alkylation, catalytic cracking, isomerization, and/or polymerization processes. During the hydrocarbon conversion process, the catalyst composition may be deactivated due to coke deposition.

The spent (i.e., deactivated) catalyst compositions are regenerated. Typically the catalyst to be regenerated comprises a molecular sieve and at least 10 wt % coke having, in embodiments, an H/C ratio in the range of 0.20 to 0.67, the process comprising:

a. contacting the catalyst composition with a first oxidative medium having oxygen and water at first conditions sufficient to form a first regenerated catalyst composition having at least 50 wt % less coke than the catalyst composition; and then b. contacting at least a portion of the first regenerated catalyst composition with a second oxidative medium having oxygen, and optionally water, at second conditions sufficient to form a second regenerated catalyst composition having at least 50 wt % less coke than the first regenerated catalyst composition, wherein the catalyst composition in step (a) and the first regenerated catalyst composition in step (b) have contacted a total amount of water in the range of 1 to 50, weight water per weight of the second regenerated catalyst composition.

In some aspects of this disclosure, the molecular sieve comprises at least one of a M41S family molecular sieve, a MCM-22 family molecular sieve, ETS-10, ETAS-10, ETGS-10, and a molecular sieve having a zeolite framework type comprising at least one of ABW, AET, AFG, AFI, AFX, ANA, AST, ASV, BCT, *BEA, BEC, BIK, BOG, BPH, BRE, CAN, CAS, CDO, CFI, CGS, CHA, -CHI, CON, DAC, DDR, DFT, DOH, DON, EAB, EDI, EMT, EON, EPI, ERI, ESV, ETR, EUO, EZT, FAR, FAU, FER, FRA, GIS, GIU, GME, GON, GOO, HEU, IFR, IHW, IMF, ISV, ITE, ITH, ITW, IWR, IWV, IWW, JBW, KFI, LAU, LEV, LIO, -LIT, LOS, LOV, LTA, LTL, LTN, MAR, MAZ, MEI, MEL, MEP, MER, MFI, MFS, MON, MOR, MOZ, MSE, MSO, MTF, MTN, MTT, MTW, MWW, NAB, NAT, NES, NON, NPO, NSI, OBW, OFF, OSO, OWE, -PAR, PAU, PHI, PON, RHO, -RON, RRO, RSN, RTE, RTH, RUT, RWR, RWY, SFE, SFF, SFG, SFH, SFN, SFO, SGT, SIV, SOD, SOS, SSY, STF, STI, STT, SZR, TER, THO, TOL, TON, TSC, TUN, UEI, UFI, UOZ, USI, UTL, VET, VNI, VSV, -WEN, and YUG.

The regenerated catalyst composition is useful as a catalyst composition in a wide range of processes, including separation processes and hydrocarbon conversion processes. Specific examples of hydrocarbon conversion processes which are effectively catalyzed by the crystalline molecular sieve(s) of this disclosure by itself or in combination with one or more other catalytically active substances including other crystalline molecular sieves, include the following:

(i) alkylation of aromatic hydrocarbons, e.g., benzene, with long chain olefins, e.g., $C_{14}$ olefin, with reaction conditions including, individually or in any combination, a temperature of from 340° C. to 500° C., a pressure of from 101 to 20200 kPa-a (absolute), a weight hourly space velocity of from 2 $hr^{-1}$ to 2000 $hr^{-1}$ and an aromatic hydrocarbon/olefin mole ratio of from 1/1 to 20/1, to provide long chain alkyl aromatics which can be subsequently sulfonated to provide synthetic detergents;

(ii) alkylation of aromatic hydrocarbons with gaseous olefins to provide short chain alkyl aromatic compounds, e.g., the alkylation of benzene with propylene to provide cumene, with reaction conditions including, individually or in any combination, a temperature of from 10° C. to 125° C., a pressure of from 101 to 3030 kPa-a, and an aromatic hydrocarbon weight hourly space velocity (WHSV) of from 5 $hr^{-1}$ to 50 $hr^{-1}$;

(iii) alkylation of reformate containing substantial quantities of benzene and toluene with fuel gas containing $C_5$ olefins to provide, inter alia, mono- and di-alkylates with reaction conditions including, individually or in any combination, a temperature of from 315° C. to 455° C., a pressure of from 3000 to 6000 kPa-a, a WHSV-olefin of from 0.4 $hr^{-1}$ to 0.8 $hr^{-1}$, a WHSV-reformate of from 1 $hr^{-1}$ to 2 $hr^{-1}$ and a gas recycle of from 1.5 to 2.5 vol/vol fuel gas feed;

(iv) alkylation of aromatic hydrocarbons, e.g., benzene, toluene, xylene and naphthalene, with long chain olefins, e.g., $C_{14}$ olefin, to provide alkylated aromatic lube base stocks with reaction conditions including, individually or in any combination, a temperature of from 160° C. to 260° C. and a pressure of from 2600 to 3500 kPa-a;

(v) alkylation of phenols with olefins or equivalent alcohols to provide long chain alkyl phenols with reaction conditions including, individually or in any combination, a temperature of from 200° C. to 250° C., a pressure of from 1500 to 2300 kPa-a and a total WHSV of from 2 $hr^{-1}$ to 10 $hr^{-1}$;

(vi) conversion of light paraffins to olefins and aromatics with reaction conditions including, individually or in any combination, a temperature of from 425° C. to 760° C. and a pressure of from 170 to 15000 kPa-a;

(vii) conversion of light olefins to gasoline, distillate and lube range hydrocarbons with reaction conditions including, individually or in any combination, a temperature of from 175° C. to 375° C. and a pressure of from 800 to 15000 kPa-a;

(viii) two-stage hydrocracking for upgrading hydrocarbon streams having initial boiling points above 260° C. to premium distillate and gasoline boiling range products in a first stage using the MCM-22 family molecular sieve of this disclosure in combination with a Groups 8-10 metal as a catalyst composition with effluent therefrom being reaction in a second stage using zeolite Beta, also in combination with a Groups 8-10 metal, as a catalyst composition, the reaction conditions including, individually or in any combination, a temperature of from 340° C. to 455° C., a pressure of from 3000 to 18000 kPa-a, a hydrogen circulation of from 176 to 1760 liter/liter and a liquid hourly space velocity (LHSV) of from 0.1 to 10 $h^{-1}$;

(ix) a combination hydrocracking/dewaxing process in the presence of the MCM-22 family molecular sieve of this disclosure and a hydrogenation component as a catalyst composition, or a mixture of such catalyst composition and zeolite Beta, with reaction conditions including, individually or in any combination, a temperature of from 350° C. to 400° C., a pressure of from 10000 to 11000 kPa-a, an LHSV of from 0.4 to 0.6 and a hydrogen circulation of from 528 to 880 liter/liter;

(x) reaction of alcohols with olefins to provide mixed ethers, e.g., the reaction of methanol with isobutene and/or isopentene to provide methyl-t-butyl ether (MTBE) and/or t-amyl methyl ether (TAM) with conversion conditions including, individually or in any combination, a temperature of from 20° C. to 200° C., a pressure of from 200 to 20000 kPa-a, a WHSV (gram-olefin per hour gram-zeolite) of from 0.1 $hr^{-1}$ to 200 $hr^{-1}$ and an alcohol to olefin molar feed ratio of from 0.1/1 to 5/1;

(xi) toluene disproportionation with $C_9$+ aromatics as co-feed with reaction conditions including, individually or in any combination, a temperature of from 315° C. to 595° C., a pressure of from 101 to 7200 kPa-a, a hydrogen/hydrocarbon mole ratio of from 0 (no added hydrogen) to 10 and a WHSV of from 0.1 $hr^{-1}$ to 30 $hr^{-1}$;

(xii) preparation of the pharmaceutically-active compound 2-(4-isobutylphenyl) propionic acid, i.e., ibuprofen, by reacting isobutyl benzene with propylene oxide to provide the intermediate 2-(4-isobutylphenyl) propanol followed by oxidation of the alcohol to the corresponding carboxylic acid;

(xiii) use as an acid-binding agent in the reaction of amines with heterocyclic fiber-reactive components in preparation of dyes to prepare practically salt-free reactive dye-containing solution, as in German Patent No. DE 3,625, 693;

(xiv) as the absorbent for separating 2,6-toluene diisocyanate (2,6-TDI) from isomers if TDI as in U.S. Pat. No. 4,721,807, whereby a feed mixture comprising 2,6-TDI and 2,4-TDI is contacted with the present MCM-22 family molecular sieve which has been cation-exchanged with K ions to absorb the 2,6-TDI, followed by recovering the 2,6-TDI by desorption with desorbent material comprising toluene;

(xv) as the absorbent for separating 2,4-TDI from its isomers as in U.S. Pat. No. 4,721,806, whereby a feed mixture comprising 2,4-TDI and 2,6-TDI is contacted with the present MCM-22 family molecular sieve which has been cation-exchanged with Na, Ca Li and/or Mg ions to absorb the 2,4-TDI, followed by recovering the 2,4-TDI by desorption with desorbent material comprising toluene;

(xvi) in a process for decreasing the durene content of a 90-200° C.+ bottoms fraction obtained from the catalytic conversion of methanol to gasoline which comprises contacting the durene-containing bottoms fraction with hydrogen over a catalyst composition of the present MCM-22 family molecular sieve with a hydrogenation metal, at conditions including, individually or in any combination, a temperature of from 230° C. to 425° C. and a pressure of from 457 to 22000 kPa-a;

(xvii) in a processes for co-producing phenol and ketones that proceed through benzene alkylation, followed by formation of the alkylbenzene hydroperoxide and cleavage of the alkylbenzene hydroperoxide into phenol and ketone, e.g., benzene and propylene to phenol and acetone, benzene and $C_4$ olefins to phenol and methyl ethyl ketone, such as those described for example in International Application No. PCT/EP2005/008557, which can be followed by conversion of phenol and acetone to bis-phenol-A as described in International Application No. PCT/EP2005/008554, benzene to phenol and cyclohexanone, or benzene and ethylene to phenol and methyl ethyl ketone, as described for example in International Application No. PCT/EP2005/008551;

(xviii) in a process of benzene alkylation reactions where selectivity to the monoalkylbenzene is required, e.g., selectively sec-butylbenzene from benzene and $C_4$ olefin feeds that are rich in linear butenes, as described in International Application No. PCT/EP2005/008557, preferably, this conversion is carried out by co-feeding benzene and the $C_4$ olefin feed with the catalyst composition of the present invention, at a temperature of 60° C. to 260° C., for example of 100° C. to 200° C., a pressure of 7000 kPa-a or less, and a feed weight hourly space velocity (WHSV) based on $C_4$ alkylating agent of from 0.1 to 50 h$^{-1}$ and a molar ratio of benzene to $C_4$ alkylating agent from 1 to 50; and (xix) in a process for transalkylations, which in a preferred embodiment, comprises contacting a feed comprising $C_9$+ aromatic hydrocarbons and at least one of toluene and benzene under transalkylation reaction conditions with a first catalyst composition comprising a zeolite having a constraint index ranging from 0.5 to 3, such as ZSM-12, and a hydrogenation component and the effluent resulting from the first contacting step is then contacted with a second catalyst composition which comprises a zeolite having a constraint index ranging from 3 to 12, such as ZSM-5, and which may be in a separate bed or a separate reactor from the first catalyst composition to produce a transalkylation reaction product comprising benzene and xylene. In another embodiment, there is a process for transalkylations, comprising contacting a feed comprising $C_9$+ aromatic hydrocarbons and at least one of toluene and benzene under transalkylation reaction conditions with a first catalyst in the presence of hydrogen under conditions effective to dealkylate aromatic hydrocarbons in the feedstock containing C2+ alkyl groups and to saturate C2+ olefins formed so as to produce a first effluent, the first catalyst comprising (i) a first molecular sieve having a Constraint Index in the range of about 3 to about 12 and (ii) at least one metal or compound thereof of Groups 6 to 12 of the Periodic Table; and then contacting at least a portion of said first effluent with a second catalyst comprising (i) a second molecular sieve having a Constraint Index less than 3 and (ii) at least one metal or compound thereof of Groups 6 to 12 of the Periodic Table under suitable transalkylation conditions effective to transalkylate C9+ aromatic hydrocarbons with said at least one C6-C7 aromatic hydrocarbon to form a second effluent comprising xylene, and optionally then contacting at least a portion of the second effluent with a third catalyst comprising a third molecular sieve having a Constraint Index in the range of about 3 to about 12.

The transalkylation process uses $C_6$-$C_7$ and $C_9$+ aromatics as fresh feeds to the unit to produce $C_8$ aromatics. As used herein the expression "$C_6$-$C_7$" means $C_6$ and/or $C_7$ aromatic hydrocarbons and $C_{9+}$ aromatics means aromatic hydrocarbons having at least 9 carbon atoms. The $C_6$-$C_7$ feed for a transalkylation process may contain up to 95 wt % of non-aromatics, which may vary in type from straight chain paraffins to naphthenes. The $C_6$-$C_7$ stream is generally processed in an extraction unit to remove the non-aromatics prior to being used in a transalkylation unit. In some cases, the extraction unit can be bypassed such that an unextracted $C_6$-$C_7$ portion is sent directly to the transalkylation unit. The unextracted $C_6$-$C_7$ feed may contain from 10 to 67 wt % $C_6$ non-aromatics and/or from 6 to 38 wt % $C_7$ non-aromatics. Some of the non-aromatics may be removed in the transalkylation unit via reactions such as cracking to lighter olefins, and subsequently saturated or alkylated with another species to form heavier molecules, or purged in downstream recovery section. The extent of the conversion depends on the type of species. Straight chain paraffins will likely react more readily than naphthenes. The unreacted non-aromatics in the $C_6$-$C_7$ feed will be recycled until extinction. Therefore, some buildup of the amount of non-aromatics in the total liquid feed to the reactor is expected, and such amount depends on the types of non-aromatics in the fresh $C_6$-$C_7$ feed.

The following experiments are intended to be representative of the present invention and should not be taken as limiting thereof.

Two samples of spent catalyst, one from the 1st load (Catalyst A) and one from the 2nd load (Catalyst B), from a commercial transalkylation reactor were obtained when the catalyst was unloaded from the reactor. Analysis of the coked catalysts showed that there was ~50% coke on catalyst from the 1st load (having a H/C ratio of 0.35) and ~35% coke on the 2nd load (estimated H/C ratio of approximately 0.55). These spent catalysts were the starting material for the regeneration studies.

EXAMPLE 1 (COMPARATIVE)

A sample of Catalyst A was loaded into a fixed bed reactor located in an isothermal furnace. The regeneration conditions used during the main burn were as follows:

| | |
|---|---|
| Average Reactor Temperature | 725-745° F. (385-396° C.) |
| Reactor Pressure | 50 psig |
| Gas Flow | 0.6 Nm$^3$/hr/kg cat |
| Inlet O$_2$ Concentration | 0.84 vol % |
| Outlet O$_2$ Concentration | 0.25 vol % |

-continued

| | |
|---|---|
| Inlet Gas H$_2$O Partial Pressure | 0.9 psia |
| Duration | 15 days |

The oxygen concentration at the exit of the reactor was monitored using an oxygen analyzer. When the conversion of oxygen dropped below 10%, a clean-up burn was used to remove any residual coke remaining on the catalyst. The conditions of the clean-up burn were as follows:

| | |
|---|---|
| Average Reactor Temperature | 806° F. (430° C.) |
| Reactor Pressure | 50 psig |
| Gas Flow | 0.6 Nm$^3$/hr/kg cat |
| Inlet O$_2$ Concentration | 7.0 vol % |
| Inlet Gas H$_2$O Partial Pressure | 0.0 psia |
| Duration | 6 hours |

Following regeneration of the catalyst, the catalytic activity for transalkylation of heavy aromatics was tested in a fixed-bed microunit. The reactor pressure was 350 psig and the H$_2$:HC ratio was 2:1. The feed to the reactor contained 85% heavy aromatics and 15% benzene+toluene. The catalyst was initially reduced in hydrogen at 427° C., then sulfided with H$_2$S prior to the introduction of feed. The reactor temperature was set to maintain an overall C$_9$+C$_{10}$ conversion of ~57.5±0.5%. The total feed flowrate, expressed as grams feed per gram catalyst per hour (WHSV) was 3 hr$^{-1}$. Product analysis occurred using on-line GC-FID with a 60 m DB-WAX column. The aging rate, expressed as the rate of increase in temperature required to maintain constant C$_9$+C$_{10}$ conversion, for the catalyst regenerated under conditions in Example 1 was 31° C./month.

EXAMPLE 2

A sample of Catalyst B was loaded into a fixed bed reactor located in an isothermal furnace. The regeneration conditions used during the main burn were as follows:

| | |
|---|---|
| Average Reactor Temperature | 725° F. (385° C.) |
| Reactor Pressure | 50 psig |
| Gas Flow | 0.6 Nm$^3$/hr/kg cat |
| Inlet O$_2$ Concentration | 0.8 vol % |
| Outlet O$_2$ Conversion | 0.3 vol % |
| Inlet Gas H$_2$O Partial Pressure | 1.0 psia |
| Duration | 15 days |

The oxygen concentration at the exit of the reactor was monitored using an oxygen analyzer. When the conversion of oxygen dropped below 10%, a clean-up burn was used to remove any residual coke remaining on the catalyst. The conditions of the clean-up burn were as follows:

| | |
|---|---|
| Average Reactor Temperature | 806° F. (430° C.) |
| Reactor Pressure | 50 psig |
| Gas Flow | 0.6 Nm$^3$/hr/kg cat |
| Inlet O$_2$ Concentration | 7.0 vol % |
| Inlet Gas H$_2$O Partial Pressure | 1.0 psia |
| Duration | 6 hours |

Following regeneration of the catalyst, the catalytic activity for transalkylation of heavy aromatics was tested in a fixed-bed microunit using the same testing protocol as described in Example 1. The aging rate, expressed as the rate of increase in temperature required to maintain constant C$_9$+C$_{10}$ conversion, for Catalyst B regenerated under the same conditions as Catalyst A, was 9.4° C./month. As indicated by this example, the state of the catalyst end of cycle impacts the aging rate by a factor of 4.

Regarding determination of the amount of coke on the catalyst and/or the H/C ratio of such coke, the method by which it is determined is not particularly important. However, whatever method is used should be used consistently. Several methods are known and representative of those are the following.

Microchemical test: a sample of coked catalyst is obtained, weighed into a nickel capsule (minimum 50 mg sample) and burned in an oxygen atmosphere. Packings and catalysts are used to make sure all the carbon combusted to CO$_2$ and to remove interfering substances (SOx, NOx, etc.). A thermal conductivity detector (TCD) was used to quantify CO$_2$ and H$_2$O which allows calculation of the amounts of H and C burned and thus the H/C ratio and coke amount.

Oxygen Analyzer. During a commercial plant catalyst regeneration the O$_2$ consumed is monitored continuously by an oxygen analyzer (commercially available), on inlet/outlet gas, and the water made is measured by that drained from the high pressure separator. It has been found that complete carbon combustion to CO$_2$ is typically the case so the amount of O$_2$ consumed and water made (drained) over the course of the regeneration can allow for a good estimation of the C and H burned. Any water added in the regeneration air (wet air) or otherwise is backed out to obtain that made from the coke combustion. Regeneration is complete when oxygen can no longer be consumed at a predetermined temperature which preferably is the maximum regeneration temperature.

More recently in-situ measuring/monitoring of catalyst coke levels and composition (H/C) useful in the present invention have been disclosed in "In situ Monitoring of Coke Deposits during Coking and Regeneration of Solid Catalysts by Electrical Impedance-based Sensors", Norbert Muller, et al., Dec. 23, 2009, Chem. Eng. Technol. 2010, 33, No. 1, 103-112; and "Real Time Control of a Catalytic Solid in a Fixed Bed Reactor Based on In-Situ Spectroscopy", S. M. Bennici, et al., Angewandte Chemie, Volume 119, Issue 28, pages 5508-5512, Jul. 9, 2007.

While the illustrative embodiments of the invention have been described with particularity, it will be understood that various other modifications will be apparent to and may be readily made by those skilled in the art without departing from the spirit and scope of the invention.

All patents, patent applications, test procedures, priority documents, articles, publications, manuals, and other documents cited herein are fully incorporated by reference for all jurisdictions in which such incorporation is permitted. When numerical lower limits and numerical upper limits are listed herein, ranges from any lower limit to any upper limit are contemplated.

What is claimed is:

1. A process for the transalkylation of a feed stream comprising C9+ aromatics and at least one of benzene and toluene, to produce xylenes, including contacting said feed stream with a catalyst comprising a molecular sieve and carrying out said contacting for a cycle time, whereby coke deposits on said catalyst during at least a portion of said cycle time and wherein the reactor temperature is increased and/or through-put is decreased over at least a portion of said cycle time in order to meet at least one predetermined indicia of conversion efficiency, the improvement comprising determining the end of cycle time by at least one of (i) wt % coke deposits on said molecular sieve, and (ii) H/C ratio of the coke deposits on said molecular sieve, wherein the end of cycle time is determined to be when the amount of coke on said catalyst is no more than 40 wt %, based on the total weight of catalyst and coke, and/or when the H/C of the coke deposits on said catalyst is no less than about 0.42, wherein said catalyst is regenerated using at least two steps, including a main burn having a predetermined inlet $O_2$ concentration, said main burn continued until the conversion of said oxygen drops below 10%, and then a clean-up burn continued for a period of time so that said catalyst has no more than 3 wt % coke, by weight of said catalyst, and wherein the regenerated catalyst has an aging rate of no more than 10.0° C./month.

2. The process of claim 1, including determining end of cycle conditions of said molecular sieve, said end of cycle conditions selected from (i) wt % coke deposits on said molecular sieve, and (ii) H/C ratio of the coke deposits on said molecular sieve; then regenerating or rejuvenation said molecular sieve and carrying out said contacting for another cycle time, with the proviso that said end of cycle conditions change from the previous cycle time; then making a determination of appropriate end of cycle conditions and operating said process based on said determination, wherein the improvement is further characterized by a decrease in molecular sieve aging rate, expressed as the rate of increase in temperature required to maintain at least one indicia of conversion efficiency constant.

3. The process of claim 1, wherein the coke on the catalyst prior to regeneration or rejuvenation has a H/C ratio in the range of 0.42 to 0.67.

4. The process of claim 1, wherein the molecular sieve catalyst is selected from Mordenite, ZSM-12, M41S, MCM-22, ZSM-5, ZSM-11, ZSM-22, ZSM-23, zeolite Beta, zeolite Y, and combinations thereof.

5. The process of claim 1, wherein the end of cycle conditions are determined by: (a) contacting said feed stream with a molecular sieve and carrying out said contacting for a cycle time, whereby coke deposits on said catalyst during at least a portion of said cycle time and wherein the reactor temperature is increased and/or through-put is decreased over at least a portion of said cycle time in order to meet at least one predetermined indicia of conversion efficiency; (b) determining end of cycle conditions, including the (i) final temperature, (ii) catalyst aging rate, and at least one of (iii) the wt % of coke deposits on said catalyst and/or (iv) the carbon to hydrogen ratio of the coke deposits on said catalyst; (c) regenerating or rejuvenating said catalyst, wherein said regenerating or rejuvenating includes removal of at least a portion of said coke deposits on said catalyst; (d) repeating steps (a) through (c) with the proviso that at least one of the end of cycle conditions in step (b) is changed; (e) determining from (d) or by repeating step (d) the desired end of cycle conditions required to increase catalyst aging rate; and then (f) operating said process under said desired end of cycle conditions.

6. The process of claim 1, wherein said molecular sieve has deposited thereon or therein 0.01 to 10 wt % of at least one of a metal element of Groups 6-10 of the Periodic Table based on the total weight of said molecular sieve and said at least one metal element prior to the deposition of coke in said process.

7. The process of claim 6, wherein said metal element is at least one of Pt, Re, Ir, and Pd.

8. The process of claim 1, wherein the regeneration or rejuvenation conditions include a regeneration or rejuvenation time sufficient to reduce the amount of said coke on said catalyst composition by at least 80 wt %.

9. The process of claim 1, wherein said process includes transalkylation of aromatic hydrocarbons, and wherein said catalyst is regenerated using at least two steps, including a main burn at reactor conditions comprising a temperature of 700-800° F. at 10-100 psig, a gas flow of from 0.1 to 1.0 $Nm^3$/hr/kg catalyst, an inlet O2 concentration of from 0.20 vol % to 1.50 vol %, and in inlet gas $H_2O$ partial pressure of from zero to 2.0 psia for a period of from 1 hour to 30 days; and then a clean-up burn at a temperature higher than the temperature in the main burn and from 750 to 850° F., with reactor pressure, gas flow, and inlet $O_2$ concentration in the same range as the main burn, with an inlet gas $H_2O$ partial pressure of from zero to 1 psia, and for a period of from 30 minutes to 24 hours.

10. The process of claim 1, wherein the end of cycle time is determined to be when the amount of coke on said catalyst is no more than 35 wt %, and/or when the H/C of the coke deposits on said catalyst is no less than 0.50.

11. The process of claim 1, wherein the coke on the catalyst prior to regeneration or rejuvenation has a H/C ratio in the range of 0.42 to 0.60.

12. The process of claim 1, wherein the coke on the catalyst prior to regeneration or rejuvenation has a H/C ratio in the range of 0.42 to 0.55.

* * * * *